United States Patent

Mitani et al.

Patent Number: 6,043,095
Date of Patent: Mar. 28, 2000

[54] METHOD OF EVALUATING SEPARATION AND EXHALATION PERFORMANCE OF VOLATILE MATTERS IN BOILING APPARATUS USED IN PRODUCTION OF BEER OR MALT LIQUORS

[75] Inventors: Yutaka Mitani; Hiroshi Akiyama; Fumito Ishida, all of Yaizu, Japan

[73] Assignee: Sapporo Breweries Limited, Tokyo, Japan

[21] Appl. No.: 09/077,313

[22] PCT Filed: Oct. 6, 1997

[86] PCT No.: PCT/JP97/03564

§ 371 Date: Jun. 4, 1998

§ 102(e) Date: Jun. 4, 1998

[87] PCT Pub. No.: WO98/15827

PCT Pub. Date: Apr. 16, 1998

[30] Foreign Application Priority Data

Oct. 9, 1996 [JP] Japan .................................. 8-285873

[51] Int. Cl.[7] .................................................. G01N 33/14
[52] U.S. Cl. ............................... 436/24; 436/119; 426/520
[58] Field of Search ...................... 436/24, 119; 426/520

[56] References Cited

PUBLICATIONS

Simon, A. T. Elimination of Dimethyl Sulphide During Low Pressure Boiling: Reduced Evaporation Rate & Its Effect on Quality & Taste of Beer. Monatsschrift For Brauwiggenschaft, 36 (7) 292–300 Abstract, 1983.

Zurcher et al. Technological Measures to Reduce the Dimethylsulphide Content of Beer. Proceedings, European Brewery Convention, 175–188 Abstract, 1979.

Nakajima et al. Effect of Wort Boiling & Treatment on the Dimethyl Sulphide Content of Wort & Beer. Brauwissschaft, 31 (9) 254–259 Abstract Only, 1978.

Primary Examiner—Randy Gulakowski
Assistant Examiner—S. Carrillo
Attorney, Agent, or Firm—Oblon, Spivak, McClelland, Maier & Neustadt, P.C.

[57] ABSTRACT

A method of evaluating a separation and exhalation performance of volatile matters present in a wort boiling apparatus used in the production of beer or malt liquors. The evaluation is conducted using a volatilization rate coefficient of dimethyl sulfide converted into a gaseous phase in boiling a wort in the boiling apparatus.

1 Claim, 6 Drawing Sheets

Type I
280 Mcal/H

Fig.3(b)

Type I
210 Mcal/H

Fig.3(c)

Type I
120 Mcal/H

Fig.4(a)

◇ FOUND VALUES
☐ CALCULATED VALUES

Type II

280 Mcal/H

Fig.5 (b)

Type II

210 Mcal/H

Fig.5 (c)

Type II

120 Mcal/H

METHOD OF EVALUATING SEPARATION AND EXHALATION PERFORMANCE OF VOLATILE MATTERS IN BOILING APPARATUS USED IN PRODUCTION OF BEER OR MALT LIQUORS

TECHNICAL FIELD

The present invention relates to a method of evaluating a separation and exhalation performance of volatile matters in a boiling apparatus used in the production of beer or malt liquors. More specifically, the present invention relates to a method of evaluating a separation and exhalation performance of volatile matters in a boiling apparatus used in the production of beer or malt liquors, in which a degree of whether or not a boiling control method of a boiling apparatus, a structure of the apparatus or the like is appropriate for separation and exhalation of volatile matters is evaluated depending on an exhalation efficiency (exhalation rate) of volatile matters in boiling a wort during the production of beer or malt liquors.

TECHNICAL BACKGROUND

In the production of beer or malt liquors, a wort producing step comprises milling a malt and a rice, a wheat, a corn, a starch and the like as secondary raw materials, reacting the mixture with an enzyme in the malt or a foreign enzyme, then removing grain husks or coagulated matters, and boiling the resulting wort in a boiling kettle (boiling apparatus) together with a hop.

In the procedure of boiling the wort, (1) a bitter taste or a flavor contained in the hop added is applied, (2) a coagulable protein in the malt is coagulated to clarify the liquid, (3) deactivation of the enzyme remaining in the wort and sterilization of the wort are conducted, and (4) removal of excess water through evaporation and removal of volatile matters which are undesirous to the flavor through volatilization and exhalation are conducted.

With respect to the degree of volatilization and exhalation of volatile matters in (4), among the above-mentioned, an evaporation rate of water has been so far employed as one standard. That is, volatile matters derived from raw materials such as a malt, a hop and the like are volatilized and exhaled in combination with evaporation of water. Further, a degree of volatilization and exhalation of these volatile matters is interpreted to be in an amount having some relationship with an evaporation rate of water.

Meanwhile, as a method of directly finding amounts of volatile matters to be volatilized and exhaled, there is a method in which an amount decreased (residual amount) of dimethyl sulfide (hereinafter abbreviated as "DMS"), one of volatile matters, in a wort after boiling is measured, and a degree of evaporation of the overall volatile matters is estimated from this measured value.

According to this method, the wort boiling condition can be evaluated from the residual amount of DMS.

However, this method could not evaluate the volatilization and exhalation efficiency of the wort with a general standard.

That is, when the volatilization and exhalation efficiency of volatile matters in the wort boiling operation is evaluated, it is required that upon unifying the boiling conditions in the boiling step, the evaluation is conducted on the basis of the amount of DMS decreased in this boiling step. When the scale and the conditions are different in each boiling apparatus, the comparative evaluation of the exhalation efficiency cannot be conducted by the above-mentioned conventional method.

The present invention aims at, for solving the above-mentioned conventional problems, analyzing the reaction and the change from formation of DMS in a wort to exhalation of the same into a gaseous phase and determining an evaluation standard which is not influenced by boiling conditions.

In other words, it is an object of the present invention to provide a method of evaluating a separation and exhalation performance of volatile matters in a boiling apparatus used in the production of beer or malt liquors, in which a degree of whether or not a boiling control method of a boiling apparatus, a structure of a boiling apparatus or the like is appropriate for separation and exhalation of volatile matters is evaluated depending on an exhalation efficiency (exhalation rate) of volatile matters in boiling a wort during the production of beer or malt liquors.

DISCLOSURE OF THE INVENTION

The present inventors have focused on the fact that the volatilization and exhalation of DMS are conducted through the consecutive procedures of formation of DMS from S-methylmethionine (hereinafter abbreviated as "SMM"), a precursor thereof, by heat reaction, and of volatilization into a gaseous phase, during the boiling of the wort. They have established the equation of the reaction rate in the consecutive procedures, and have inserted therein the measured values of amounts of SMM and DMS formed during the boiling of the wort to calculate the "reaction rate coefficient" and the "volatilization rate coefficient" in each consecutive procedures. Then, they have found that the volatilization rate coefficient among them increases depending on the heat supply rate in the boiling and varies depending on the shape of the boiling apparatus. That is, as the heat supply rate is increased, the wort in the boiling apparatus flows vigorously, the degree of contact between the wort and the gaseous phase is increased, and the volatile matters from the wart are volatilized and exhaled more easily, thereby increasing the volatilization rate coefficient. Further, even at the same heat supply rate, volatile matters are volatilized and exhaled more easily with a boiling apparatus in which a wart is actively mixed with flowing and the gas-liquid contact is vigorously conducted, increasing the volatilization rate coefficient.

From these facts, it is possible to evaluate the efficiency of volatilization and exhalation of volatile matters of wort boiling procedure or from the wart boiling apparatus by comparison in the volatilization rate coefficient of the volatile matters. However, from the strict viewpoint of the reaction rate, not only is the coefficient of exhalation during the volatilization and exhalation of DMS compared in the evaluation of the efficiency of volatilization and exhalation of DMS, but also is it necessary to consider the formation through conversion from SMM to DMS which is the preceding procedure. However, this formation of DMS tends to be increased chiefly depending on the temperature. Accordingly, in the wart boiling procedure in which the wart remains almost unchanged at the boiling point, almost no change can be observed. Therefore, the volatilization rate coefficient is the first factor through which to determine the efficiency of exhalation.

Accordingly, the present invention is to provide a method of evaluating a separation and exhalation performance of volatile matters in a boiling apparatus used in the production of beer or malt liquors, characterized in that the evaluation is conducted using a volatilization rate coefficient of dimethyl sulfide (DMS) into a gaseous phase in boiling a wort of the boiling apparatus.

BRIEF DESCRIPTION OF DRAWINGS

FIGS. 3(a), 3(b) and 3(c) show results depending on heat supply rate conditions of three grades, 280 Mcal/H, 210 Mcal/H and 120 Mcal/H respectively.

FIGS. 4(a), 4(b) and 4(c) show results depending on heat supply rate conditions of three grades, 280 Mcal/H, 210 Mcal/H and 120 Mcal/H respectively.

FIGS. 5(a), 5(b) and 5(c) show results depending on heat supply rate conditions of three grades, 280 Mcal/H, 210 Mcal/H and 120 Mcal/H respectively.

FIGS. 6(a), 6(b) and 6(c) show results depending on heat supply rate conditions of three grades, 280 Mcal/H, 210 Mcal/H and 120 Mcal/H respectively.

In FIGS. 1 to 7, numeral 1 is a wort boiling kettle, numeral 2 a heat exchanger, numeral 2A an end, numeral 2B a cylindrical portion, numeral 3 a heating tube, and numeral 4 a spreader respectively.

BEST MODE FOR CARRYING OUT THE INVENTION

The present invention is described below.

The present invention is characterized in that as described below, the DMS consecutive exhalation procedure is analyzed in view of the reaction rate and the DMS exhalation efficiency in the boiling step is obtained as a volatilization rate coefficient whereby the performance of separation and exhalation of volatile matters in the boiling apparatus can be evaluated.

It has been known from the past reports that the reaction behaviors of DMS in boiling the wort are mainly formation of it from SMM which is a DMS precursor and its exhalation into a gaseous phase [for example, J. Inst. Brew. 88, p. 244 (1982), Anness, B. J. and Bamforth, C. W. (1982)].

That is, SMM is not formed in boiling the wort, and an amount of dimethyl sulfoxide (DMSO) or the like converted from DMS is small. Accordingly, the following consecutive steps can be drawn.

SMM→DMS→(exhalation into a gaseous phase)

(reaction of formation in a gaseous phase)

The reaction rate and the exhalation rate in the consecutive steps are assumed as described in the following equations respectively.

$r_1 = k_1[S]$ $r_2 = k_2([D]_L - [D]_G)$ wherein $r_1$ is a rate of conversion from SMM to DMS ($\mu$mol/L·min), $r_2$ is an exhalation rate of DMS ($\mu$mol/L·min), $k_1$ is a reaction rate coefficient (1/min), $k_2$ is a volatilization rate coefficient (1/min), [S] is a concentration of SMM in a liquid phase ($\mu$mol/L), $[D]_L$ is a concentration of DMS in a liquid phase ($\mu$mol/L), and $[D]_G$ is a concentration of DMS in a gaseous phase ($\mu$mol/L).

The concentration of DMS in the gaseous phase is a value obtained by calculating a gas partial pressure of DMS in the gaseous phase in terms of a concentration in the liquid phase which corresponds thereto.

In this assumption, the conversion of SMM to DMS only depends on the SMM concentration of the liquid phase, and the rate equation can be expressed by a first-order reaction. In the exhalation rate of DMS, the difference between the DMS concentrations in the gaseous phase and in the liquid phase is a driving force. Accordingly, the decrease rates of SMM and DMS are rewritten as in the following equations.

$$d[S]/dt = -k_1[S] \tag{1}$$

$$d[D]_L/dt = k_1[S] - k_2([D]_L - [D]_G) \tag{2}$$

The solution of the equation (1) is:

$$[S]/[S]_0 = \exp(-k_1 t) \tag{3}$$

wherein $[S]_0$ is an SMM concentration in a liquid phase when starting the reaction ($\mu$mol/L).

Therefore, the equation (2) is:

$$d[D]_L/dt = k_1[S]_0 \exp(-k_1 t) - k_2[D]_L + k_2[D]_G \tag{4}$$

Since DMS in the gaseous phase is always discharged outside of the system, DMS is seemed to be approximately constant at quite a low concentration; then, the equation (4) can be treated as a first order linear differential equation. The solution thereof is:

$$[D]_L = \exp(-\int k_2 dt)[\int \{k_1[S]_0 \exp(-k_1 t) + k_2[D]_G\} \cdot \exp(\int k_2 dt)dt + C] \tag{5}$$

wherein C is an integration constant.

The solution of the equation (5) is:

$$[D]_L = \{k_1/(k_2 - k_1)\}[S]_0 \exp(-k_1 t) + [D]_G + C \exp(-k_2 t) \tag{5'}$$

Needless to say, since the wort concentration or the efficiency of gas-liquid contact varies before or after the boiling, the exhalation rate of volatile matters varies. What matters in the present invention is the wort during the boiling. Therefore, the time when the wort reaches boiling point is regarded as "0" hour (t=0). Thus, the concentrations of SMM and DMS at the time when the wort reaches boiling point are represented as follows respectively.

$[S] = [S]_0$ $[D]_L = [D]_{L0}$

C is calculated by inserting the above-mentioned into the equation (5)' as follows.

$$C = [D]_{L0} - [\{k_1/(k_2 - k_1)\}[S]_0 + [D]_G] \tag{6}$$

The equation (6) is inserted into the equation (5) as follows.

$$[D]_L = \{k_1/(k_2-k_1)\}[S]_0 \exp(-k_1 t) + [D]_G + \{[D]_{L0} - \{k_1/(k_2-k_1)\}[S]_0 - [D]_G\} \exp(-k_2 t) \quad (7)$$

In practice, the DMS concentration in the liquid phase is low in the order of $\mu$mol per liter. Further, since the gaseous phase is always discharged as mentioned earlier, the DMS level in the gaseous phase is considered to be too low to become a gas-liquid transfer resistance.

That is, in the equation (7), $$[D]_G \approx 0$$

Then, the DMS concentration in the liquid phase is provided as described in the following equation.

$$[D]_L = \{k_1/(k_2-k_1)\}[S]_0\{\exp(-k_1 t) - \exp(-k_2 t)\} + [D]_{L0} \exp(-k_2 t) \quad (8)$$

As mentioned above, the SMM concentration and the DMS concentration in the liquid phase lead to the equations (3) and (8), respectively.

That is, the decrease rate of the SMM concentration, namely, the rate of formation by conversion from SMM to DMS is represented by the equation (3). Therefore, the logarithmic value of $([S]/[S]_0)$ is plotted against the boiling time, and the coefficient $k_1$ of the reaction rate is calculated from the linear inclination having this point interpolated therein as an approximate solution.

Further, the change in the DMS concentration, namely, the amount of DMS formation from SMM and decreased by volatilization and exhalation is represented by the equation (8). In the equation (8), $[D]_L$, $[D]_{L0}$ and $[S]_0$ are obtained by measuring the amounts of DMS and SMM in the wart, and the reaction rate coefficient $k_1$ is experimentally calculated from the above-mentioned equation (3). However, the equation (8) is non-linear, and the volatilization rate coefficient $k_2$ is not calculated by simply inserting the same. However, the approximate solution can be obtained by applying a numerical solution method such as a Runge-Kutta method.

The present invention is illustrated more specifically by referring to the following Examples. However, the present invention is not limited thereto.

EXAMPLE 1

Figure 1:
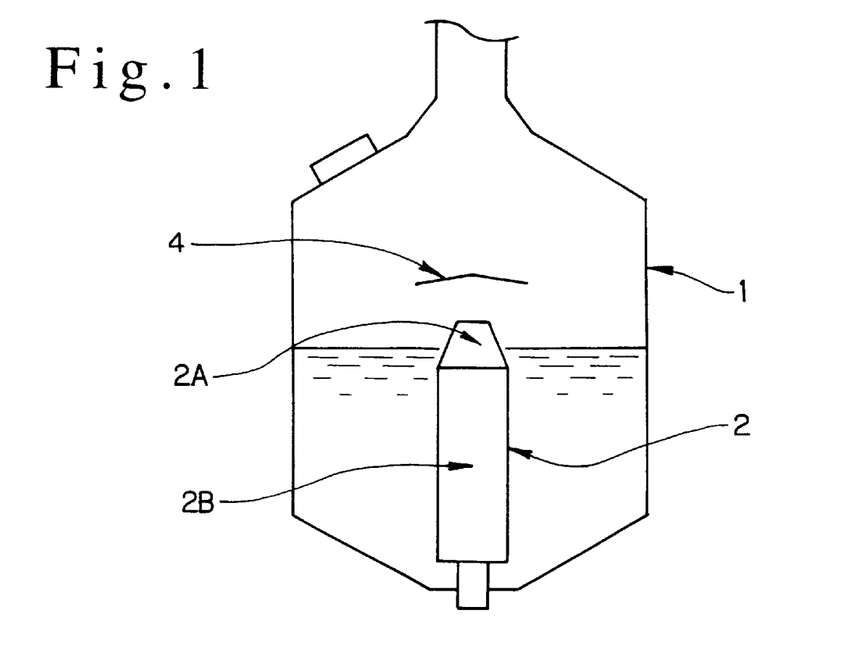
FIG. 1 is a descriptive view showing an example of a structure of a boiling apparatus used in the method of the present invention.
Figure 2:
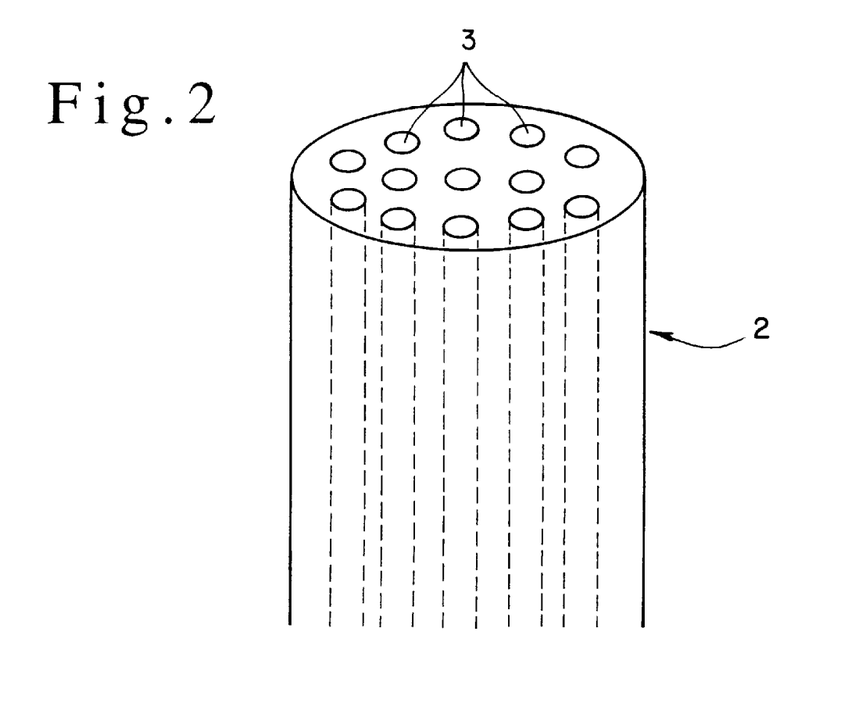
FIG. 2 is a descriptive view showing a structure of a cylindrical portion in the boiling apparatus shown in FIG. 1.

An example of the structure of the boiling apparatus used in the method of the present invention is shown in FIG. 1. This boiling apparatus comprises a wort boiling kettle 1 for accumulating a wort to be boiled, a heater (hereinafter referred to as a "heat exchanger 2") for boiling a wart which is mounted within the kettle 1 and a spreader 4 for returning a wart bumped from the top of the heat exchanger 2 to a wort accumulated in the wart boiling kettle 1. The heat exchanger 2 comprises a conical top 2A and a cylindrical portion 2B. The structure of the cylindrical portion 2B is, as shown in FIG. 2, provided with a plurality of heating tubes 3. Hot water, a high-temperature steam or a high-temperature heat medium flowed around the heating tubes 3 to heat the wart filled within the boiling apparatus to the boiling point. The wort which reached the boiling point is bumped with the heating tubes 3, and circulated within the apparatus in the order, inside of the kettle→heat exchanger (heating tubes)→spreader→wort liquid level→bottom of the kettle. In the heat exchanger 2, the outer diameter of the cylindrical portion is 430 mm, the length of the heating tube 1,280 mm, the inner diameter of the heating tube: 34.5 mm, the number of the heating tubes: 20, and the total heating area of the heating tube: 2.77 mm$^2$, respectively.

After the wort was filled in the wort boiling kettle of the boiling apparatus, the heating started, and the heat supply rate was maintained at 210 Mcal/H until the boiling started. After the boiling started, this boiling was conducted under three-grade heat supply rate conditions, 280 Mcal/H, 210 Mcal/H and 120 Mcal/H.

The specimen was collected before the wort temperature raised, 10 minutes before the wort reached boiling point, at the time when the wort reached boiling point, 5 minutes after the boiling point and 15 minutes after the boiling point, and the SMM concentration and the DMS concentration were measured.

Figure 3A:
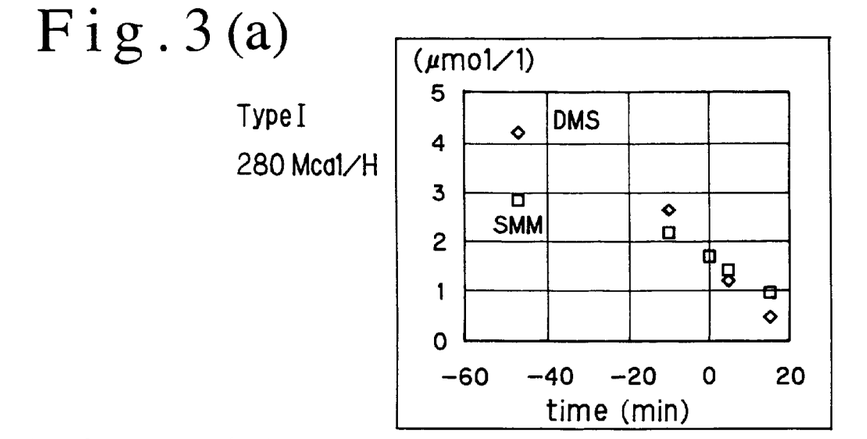
FIGS. 3(a), (b) and (c) are graphs showing the change in the SMM concentration and the change in the DMS concentration in the case where the time when the wort reaches boiling point is regarded as 0 in the boiling apparatus type I.
Figure 3B:
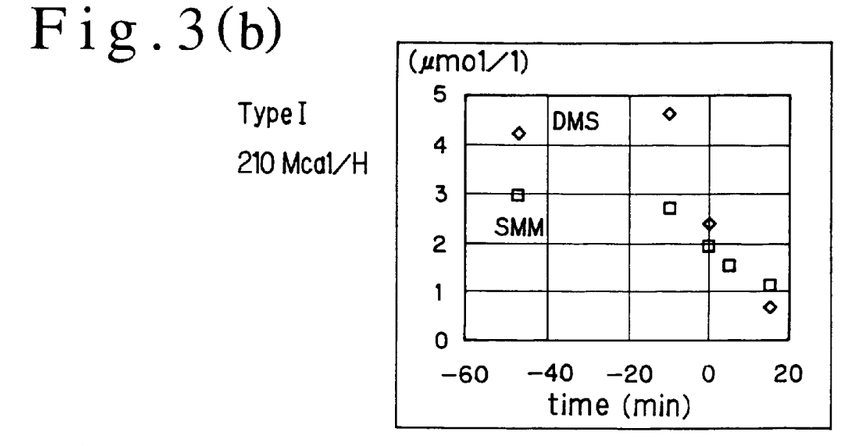
Figure 3C:
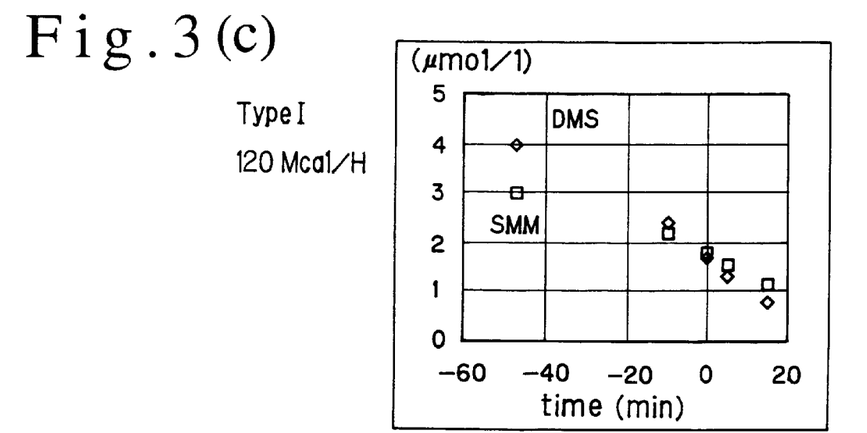

The change in the SMM concentration and the change in the DMS concentration in the case where the time when the wort reaches boiling point is regarded as 0 are shown in FIGS. 3(a), 3(b) and 3(c). FIGS. 3(a), 3(b) and 3(c) show the results according to the three-grade heat supply rate conditions, 280 Mcal/H, 210 Mcal/H and 120 Mcal/H.

The conversion reaction rate coefficient $k_1$ from SMM to DMS was found by four time points from 10 minutes before the boiling point on the basis of the thus-obtained SMM concentrations using the equation (3). That is, the logarithmic value of $([S]/[S]_0)$ was plotted, and the linear inclination having this point therein was calculated through the linear approximation by the least square method.

The thus-obtained conversion reaction rate coefficient $k_1$ is shown in Table 1 (type I).

Subsequently, the volatilization rate coefficient $k_2$ was found from the thus-obtained conversion reaction rate coefficient $k_1$ and the DMS measured value of the wort using the Runge-Kutta method, one of numerical solution methods.

Figure 4A:
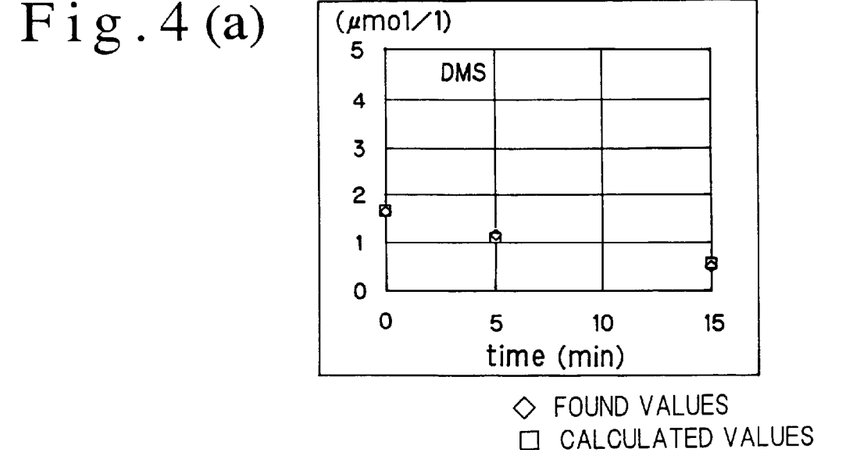
FIGS. 4(a), (b) and (c) are graphs showing DMS found and calculated values in the boiling apparatus type I.
Figure 4B:
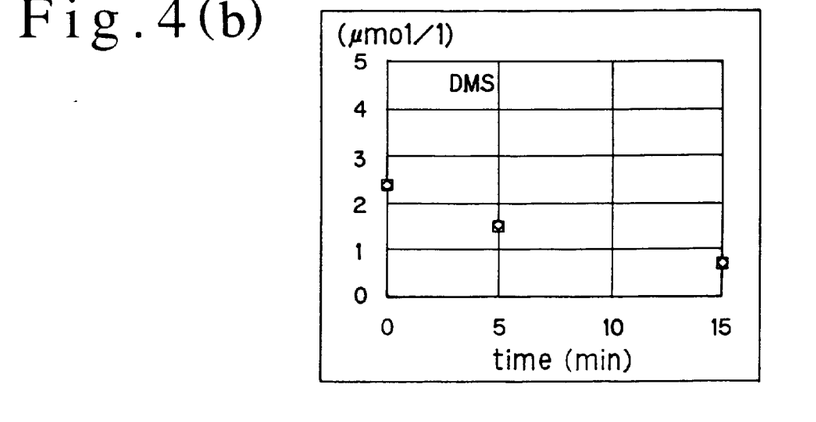
Figure 4C:
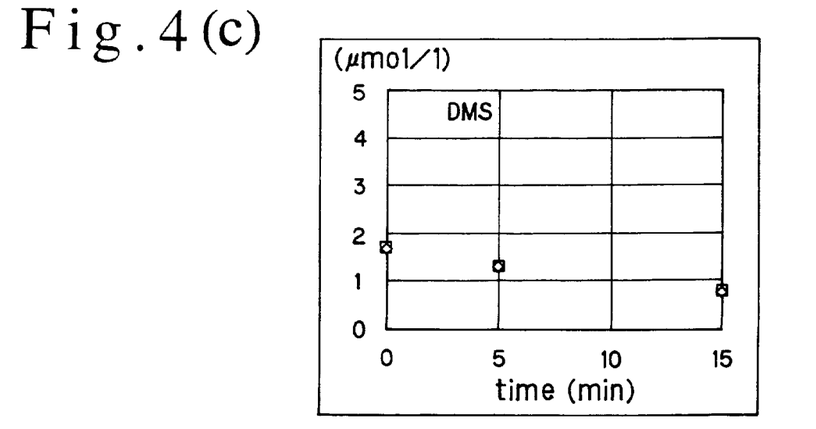

The approximate solution of the thus-obtained volatilization rate coefficient $k_2$ is shown in Table 2 (type I). The comparison between the DMS value obtained by inserting this approximate solution into the equation (8) and the found results of the wort boiled is shown in FIGS. 4(a), (b) and (c). FIGS. 4(a), 4(b) and 4(c) show the results according to the three-grade heat supply rate conditions, 280 Mcal/H, 210 Mcal/H and 120 Mcal/H, respectively. Both plots are coincident well with each other, and it is found that the approximate solution obtained by the numerical solution method using the equation (8) is reasonable.

EXAMPLE 2

Example 1 was repeated except that the following type II was used instead of the type I as a boiling apparatus.

The difference between the boiling apparatus type II in this Example and the boiling apparatus type I in Example 1 is in the type of the heat exchanger 2. That is, the heat exchanger 2 is different in that a length of a heating tube is 804 mm, an inner diameter of the heating tube: 44.8 mm, the number of heating tubes: 24, and the total heating area of the heating tubes: 2.72 mm$^2$, respectively. In comparison with Example 1, Example 2 uses a heating portion which is thick and short.

Figure 5A:
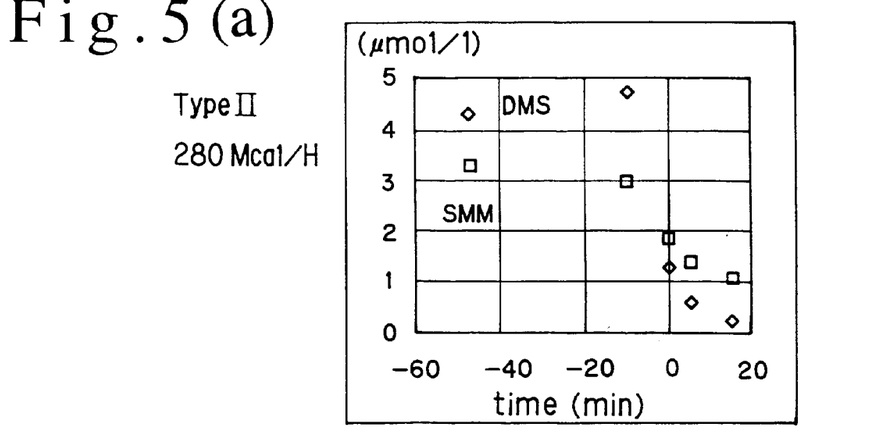
FIGS. 5(a), (b), and (c) are graphs showing the change in the SMM concentration and the change in the DMS concentration in the case where the time when the wort reaches boiling point is regarded as 0 in the boiling apparatus type II.
Figure 5B:
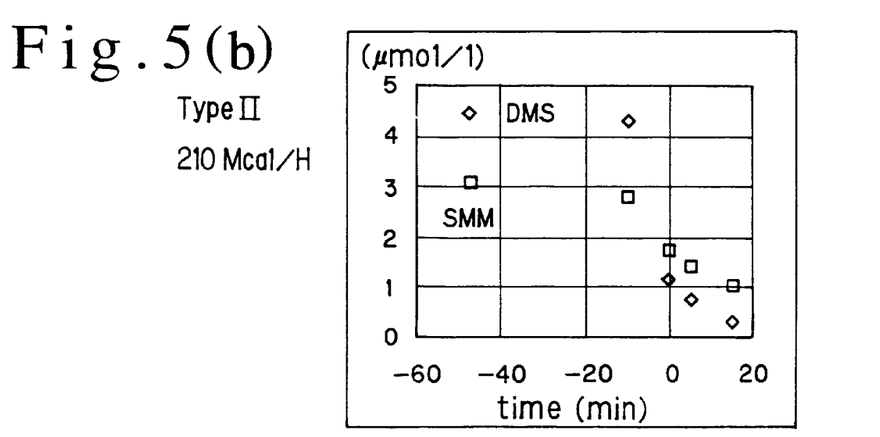
Figure 5C:
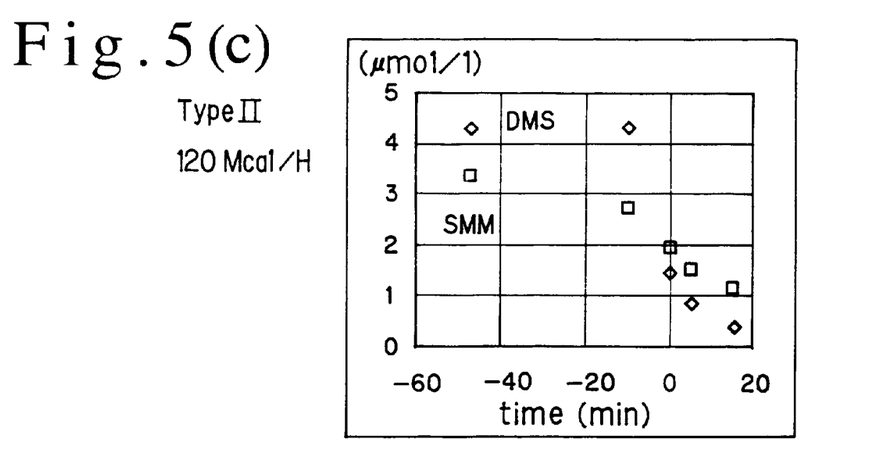
Figure 6A:
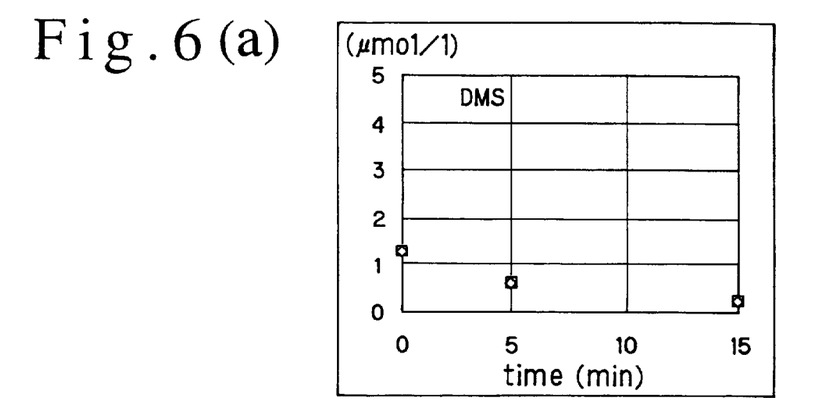
FIGS. 6(a), (b) and (c) are views showing DMS found and calculated values in the boiling apparatus type II.
Figure 6B:
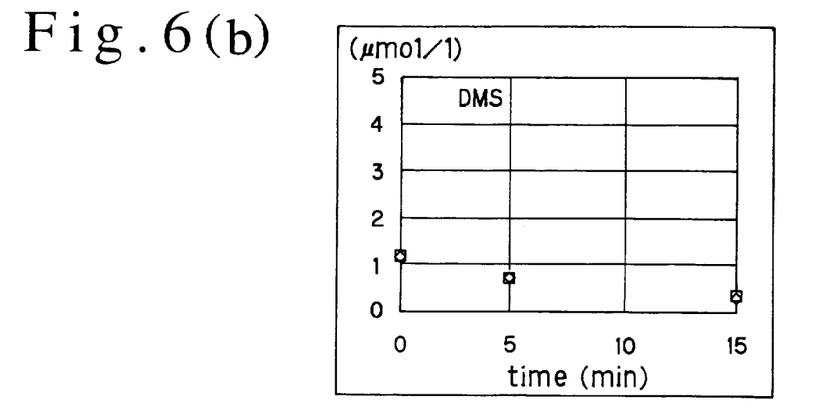
Figure 6C:
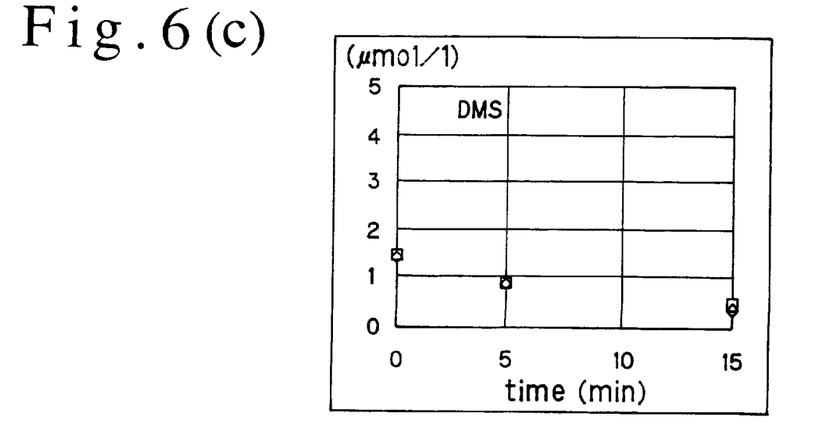

The found values of the change in the SMM concentration and the change in the DMS concentration in the boiling apparatus type II are shown in FIGS. 5(a), 5(b) and 5(c). The thus-obtained conversion reaction rate coefficient $k_1$ is shown in Table 1 (type II). Further, the volatilization rate coefficient $k_2$ was found as in Example 1. The results are shown in Table 2 (type II). The comparison between the calculated values and the found values of DMS is shown in FIGS. 6(a), (b) and (c). FIGS. 6(a), 6(b) and 6(c) show the results according to the three-grade heat supply rate conditions, 280 Mcal/H, 210 Mcal/H and 120 Mcal/H. Both are quite approximate as in Example 1.

TABLE 1

| Type of a wort boiling kettle | Heat supply rate (Mcal/H) | $k_1$(/min) |
|---|---|---|
| I | 280 | 0.0321 |
| I | 210 | 0.0347 |
| I | 120 | 0.0259 |
| II | 280 | 0.0413 |
| II | 210 | 0.0390 |
| II | 120 | 0.0344 |

TABLE 2

| Type of a wort boiling kettle | Heat supply rate (Mcal/H) | $k_2$(/min) |
|---|---|---|
| I | 280 | 0.121 |
| I | 210 | 0.125 |
| I | 120 | 0.087 |
| II | 280 | 0.238 |
| II | 210 | 0.168 |
| II | 120 | 0.162 |

Figure 7:
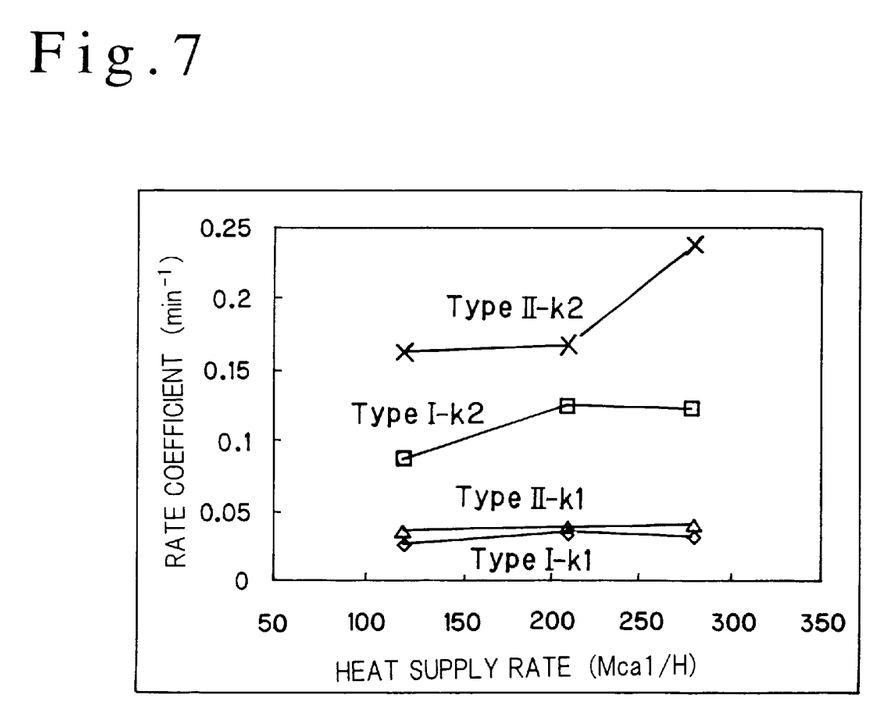
FIG. 7 is a graph of comparison with respect to the relationship of the reaction rate coefficient ($k_1$) from SMM to DMS and the over-all volatilization rate coefficient ($k_2$) of the DMS to the shape of the wort boiling kettle and the heat supply rate.

The results in Tables 1 and 2 were graphically represented, and the comparison (analysis) was conducted with respect to the relationship between the reaction rate coefficient ($k_1$) from SMM to DMS and the over-all volatilization rate coefficient ($k_2$) of DMS on one hand and the shape of the wart boiling kettle and the heat supply rate on the other. The results are shown in FIG. 7.

As mentioned above, the reaction behaviors of DMS in boiling the wort were mainly the formation of DMS from SMM and the exhalation thereof into the gaseous phase. The equations of the reaction rates were established as the reaction rate coefficient ($k_1$) in the reaction of SMM→DMS and the volatilization rate coefficient ($k_2$) in the DMS→exhalation. The measured data of the residual amount of DMS in the wort was inserted therein to give the respective coefficients. In the measurement, the rate coefficients were compared with respect to the change (three grades) in the heat supply rate of the boiling apparatus [heat supply rate after the boiling point (when the wort reached the boiling point)] and the difference in the shape of the apparatus.

The reaction rate coefficient ($k_1$) from SMM to DMS is scarcely influenced by the shape of the wort boiling kettle and the change in the heat supply rate. This is presumably because the conversion reaction depends only on the temperature (because the wort temperature is maintained at the boiling point when the heat supply rate is more than the predetermined rate). That is, it is found that the reaction rate coefficient ($k_1$) does not depend on the heat supply rate and the shape of the apparatus.

On the other hand, the volatilization rate coefficient ($k_2$) of DMS in the boiling apparatus type II is higher than that in the boiling apparatus type I, and it is increased according to the increase in the heat supply rate. Thus, it becomes clear that this coefficient highly depends on both of the shape of the wort boiling kettle and the heat supply rate. That is, the above-mentioned anticipation was supported that the higher the ($k_2$) value rises, the better the exhalation rate of the volatile matters in the boiling apparatus becomes.

Even in the state of the same heat supply rate, the volatilization rate coefficient $k_2$ in the boiling apparatus type II is higher than that in the boiling apparatus type I. That is, the coefficient of exhalation of the volatile matters is higher in the type II presumably because the number of the heating tubes is larger and the length of the tube is shorter so that the amount, per unit time, of the wort injected from the heat exchanger 2 is increased and the gaseous phase in the wort boiling kettle 1 is often brought into contact with the wort more often.

The water in the wort is evaporated with a heat supplied within the heating tube, and it becomes a steam to increase the volume, whereby the wort is injected outside of the heater. This injection stream is important to activate the mixing of the wort with flowing. Accordingly, it is not necessarily good to simply shorten the length of the heating tube, and the heating tube is required to have a heat-exchangeability to such an extent that the jet stream of the wort is kept at a fixed level.

The boiling apparatus type II has a good efficiency of DMS exhalation presumably because it provides a larger amount of gas-liquid contact than the boiling apparatus type II even at the same heat supply rate.

From the above-mentioned analytical results, the volatilization rate coefficient in the boiling apparatus was found, and the absolute value thereof was studied by comparison, with the result that the performance of separation and exhalation in the boiling apparatus could be estimated.

Therefore, according to the present inventions, it is possible to relatively evaluate (evaluate superiority or inferiority by comparison) with a use of "over-all volatilization rate coefficient", whether the apparatus is appropriate in the separation and exhalation of volatile matters concerning the boiling control method of the boiling apparatus, the structure of the apparatus and the like.

According to the present invention, relative evaluation of whether or not a boiling apparatus is itself appropriate for separation and exhalation of volatile matters upon using an exhalation rate coefficient in view of a boiling control method of the boiling apparatus, a structure of the apparatus and the like.

Thus, volatile matters which are undesirous to the flavor of products can be volatilized more efficiently using the boiling apparatus in which excellent results are obtained by the evaluation method of the present invention.

Industrial Applicability

The exhalation efficiency of volatile matters in the boiling apparatus is evaluated by the evaluation method of the present invention, whereby the exhalation performance of volatile matters which are undesirous to the flavor can be improved. Accordingly, beer or malt liquors having a better taste can be obtained.

I claim:

1. A method of evaluating a separation and exhalation performance of volatile matter in a wort boiling process used in the production of beer or malt liquors, comprising the steps of:

a) measuring the concentration of S-methylmethionine and the concentration of dimethyl sulfide in the wort during boiling of the wort;

b) determining a conversion reaction rate coefficient from the conversion of S-methylmethionine to dimethyl sulfide;

c) determining a volatilization rate coefficient from said conversion reaction rate coefficient and the concentration of dimethyl sulfide in the wort; and d) correlating the volatilization rate coefficient to the separation and exhalation performance of volatile matter in the wort boiling process.

* * * * *